United States Patent [19]

Laidler et al.

[11] 4,344,894

[45] Aug. 17, 1982

[54] PROCESS FOR THE PREPARATION OF CYCLOPROPANE CARBOXYLIC ACID ESTERS

[75] Inventors: Dale A. Laidler, Chester; David J. Milner, Manchester, both of England

[73] Assignee: Imperial Chemical Industries Limited, London, England

[21] Appl. No.: 156,076

[22] Filed: Jun. 2, 1980

[30] Foreign Application Priority Data

Jul. 13, 1979 [GB] United Kingdom ............... 7924522

[51] Int. Cl.$^3$ ............... C07C 120/00; C07C 67/347
[52] U.S. Cl. ............... 260/465 D; 252/431 N; 536/4; 536/18; 536/121; 542/414; 542/422; 542/424; 560/124
[58] Field of Search ............... 560/124; 260/465 D

[56] References Cited

U.S. PATENT DOCUMENTS

| | | | |
|---|---|---|---|
| 3,868,401 | 2/1975 | Arakani | 560/124 |
| 4,069,385 | 1/1978 | Araki | 560/124 |
| 4,197,408 | 4/1980 | Avatani | 560/124 |

FOREIGN PATENT DOCUMENTS

| | | | |
|---|---|---|---|
| 50-157349 | 12/1975 | Japan | 560/124 |
| 50-160241 | 12/1975 | Japan | 560/124 |
| 52-34616 | 5/1977 | Japan | 560/124 |
| 52-34617 | 5/1977 | Japan | 560/124 |
| 740014 | 11/1955 | United Kingdom . | |
| 1455189 | 11/1976 | United Kingdom . | |

*Primary Examiner*—Michael L. Shippen
*Attorney, Agent, or Firm*—Cushman, Darby & Cushman

[57] ABSTRACT

3-(Halogenovinyl- or propenyl-)-2,2-dimethyl cyclopropane-1-carboxylic acid esters, which are precursors of, or may themselves be, pyrethroid insecticides, are prepared by the reaction of certain halogenopentadienes with an alkyl diazoacetate in the presence of a catalyst which is a transition metal complex of certain chiral Schiff bases, which catalysts tend to increase the yield of preferred cis IR isomer relative to the other possible isomers.

1 Claim, No Drawings

PROCESS FOR THE PREPARATION OF CYCLOPROPANE CARBOXYLIC ACID ESTERS

This invention relates to a chemical process and more particularly to a process for the preparation of 3-(halogenovinyl- or propenyl)-2,2-dimethylcyclopropane-1-carboxylic acid esters which are precursors of, or may themselves be, synthetic pyrethroid insecticides.

It is known from United Kingdom Patent Specification No. 740,014 to react an alkyl diazoacetate with 2,5-dimethylhexa-2,4-diene in the presence of a copper catalyst to give an alkyl ester of chrysanthemic acid.

Also, United Kingdom Patent Specification No. 1455189 discloses the asymmetric synthesis of alkyl chrysanthemates by reacting 2,5-dimethylhexa-2,4-diene with an alkyl diazoacetate in the presence of catalysts which are copper complexes of certain chiral Schiff bases.

Belgian Patent Specification No. 863151 discloses the preparation of compounds of the formula:

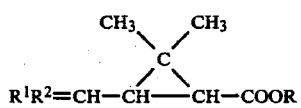

wherein R is a lower alkyl group and $R^1$ and $R^2$ are such that, inter alia, one of $R^1$ and $R^2$ represents a trifluoromethyl group and the other represents a halogen atom, by reacting a diene of formula $R^1R^2=CH—CH=C(CH_3)_2$ with a lower alkyl ester of diazoacetic acid. This reaction is conveniently conducted using an excess of the diene as a solvent for the alkyl diazoacetate in the presence of a metallic catalyst, for example, powdered copper or copper bronze.

It has now been found that this reaction can be extended to the use of certain novel chiral catalysts, with beneficial results.

According to the present invention there is provided a process for the preparation of a compound of the formula:

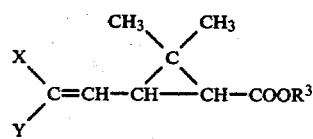 (I)

wherein $R^3$ is an alkyl, 3-phenoxybenzyl, α-cyano-3-phenoxybenzyl or α-ethynyl-3-phenoxybenzyl group and X and Y, which may be the same or different, are fluorine, chlorine, bromine, lower alkyl or $Q(CF_2)_m—$, in which Q is hydrogen, fluorine or chlorine and m is 1 or 2, or

in which each of U, V and W are independently hydrogen, fluorine or chlorine except that where one of X and Y is a group of formula $Q(CF_2)_m—$ where Q is as defined above, the other of X and Y is fluorine, chlorine or bromine or a group

as previously defined, which comprises reacting a compound having the formula:

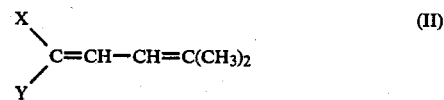 (II)

with an alkyl diazoacetate $N_2CH.COOR^3$, $R^3$, X and Y having the previously defined meanings, in the presence of a catalyst selected from the following classes (i) to (iii)

(i) the transition metal complex of a chiral Schiff base having the general formula:

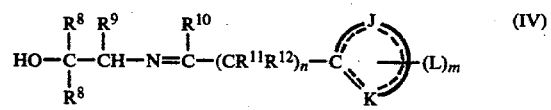 (IV)

wherein $R^8$ and $R^9$, which may be the same or different, are alkyl, aralkyl or aryl;

$R^{10}$ is hydrogen, lower alkyl, aryl, aralkyl or alkaryl;

$R^{11}$ and $R^{12}$, which may be the same or different are hydrogen or lower alkyl, or where n is 1, may with the cyclic system to which $CR^{11}R^{12}$ is attached, form a fused ring system, J is a chain of 3 or 4 atoms consisting either exclusively of carbon atoms or of carbon atoms together with one or more hetero-atoms which may be the same or different, which chain with the group —C=====K— forms an aromatic system, K is nitrogen, N→O or —NH—, L, each of which may be the same or different, represents a substituent attached to a carbon atom in the chain J and is hydrogen, alkyl, aralkyl, aryl or a substituent containing a hetero-atom, or two groups L together with the ring to which they are attached, form a fused ring system, n is 0, 1 or 2, and m is the number of carbon atoms in the chain J, (ii) the transition metal complex of a chiral Schiff base having the general formula:

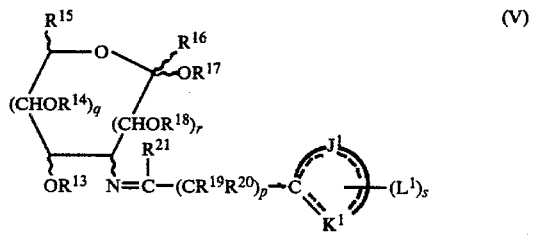 (V)

wherein $R^{13}$, $R^{14}$, and $R^{18}$, which may be the same or different, are hydrogen or lower alkyl, except that at least one of $R^{13}$ and $R^{18}$ is hydrogen, $R^{15}$ is hydrogen, a sugar derivative or —$CH_2OR^{22}$ in which $R^{22}$ is hydrogen, lower alkyl or together with $R^{14}$ forms a divalent hydrocarbon group, $R^{16}$ is hydrogen or —$CH_2OH$, $R^{17}$ is hydrogen, lower alkyl or a sugar derivative, $R^{19}$ and $R^{20}$, which may be the same or different, are hydrogen or lower alkyl, or where p is 1, may with the cyclic system to which $CR^{19}R^{20}$ is attached form a fused ring system, $R^{21}$ is hydrogen, alkyl, aralkyl or aryl, $J^1$ is a chain of 3 or 4 atoms consisting either exclusively of carbon atoms or of carbon atoms together with one or more hetero atoms which may be the same or different, which chain with the group —C$=\!=\!=$K— forms an aromatic system, K is C—OH, nitrogen, N→O or —NH—, $L^1$, each of which may be the same or different, represents a substituent attached to a carbon atom in the chain $J^1$ and is hydrogen, alkyl, aralkyl, aryl or a substituent containing a heteroatom, or two groups $L^1$ together with the ring to which they are attached form a fused ring system, r is 0 or 1, q is 0, 1 or 2, provided that q+r is 1, 2 or 3, p is 0, 1 or 2, and s is the number of carbon atoms in the chain $J^1$, and (iii) the transition metal complex of a chiral Schiff base having the general formula:

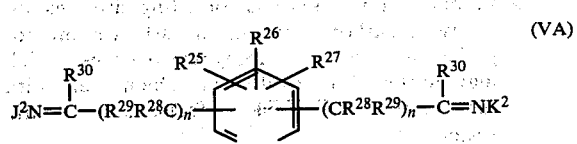
(VA)

wherein $R^{25}$, $R^{26}$ and $R^{27}$, which may be the same or different, are hydrogen, alkyl, aralkyl, aryl, a substituent containing a hetero atom, or two of $R^{25}$, $R^{26}$ and $R^{27}$ together with the pyridine ring from a fused ring system, $R^{28}$ and $R^{29}$, which may be the same or different, are hydrogen, lower alkyl, or, where n is 1, may with the pyridine ring to which $CR^{28}R^{29}$ is attached, form a fused ring system, $R^{30}$ is hydrogen, alkyl, aralkyl or aryl, n is 0, 1 or 2 and $J^2$ and $K^2$, which may be the same or different, are groups of the formulae:

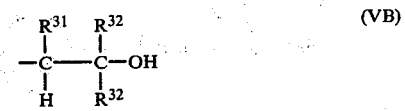
(VB)

or

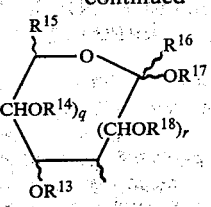
(VC)

in which $R^{31}$ and $R^{32}$, which may be the same or different, are alkyl, aralkyl or aryl, and $R^{13}$, $R^{14}$, $R^{15}$, $R^{16}$, $R^{17}$, $R^{18}$, q and r have the previously defined meanings, and the corresponding compounds having an oxygen atom attached to the pyridine ring nitrogen.

In the above definition the term "lower alkyl" means an alkyl group containing up to 5 carbon atoms.

The process according to the present invention is preferably carried out in the presence of an inert solvent in which the cyclopropane product of formula (I) is soluble.

Conveniently the solvent used is immiscible with water to facilitate preparation of the diazoacetic ester. More preferably the solvent also has a boiling point lower than that of the diene of formula (II) to facilitate recovery of unreacted diene.

Suitable solvents include saturated chlorinated hydrocarbon solvents, such as ethylene dichloride, dichloromethane, tetrachloroethane and carbon tetrachloride, and hydrocarbon solvents such as toluene.

The concentration of catalyst in the reaction mixture is not critical, but generally concentrations equivalent to 0.00001 to 1 g atoms of transition metal per liter of reaction mixture, and especially 0.005 to 1 g atoms, are suitable. The temperature of reaction is generally in the range 0° to 130° C., preferably 10° C. to 90° C.

The diazoacetic acid ester may be prepared by reacting a water soluble acid addition salt (e.g. the hydrochloride) of an ester of glycine with an alkali metal nitrite in an aqueous medium, which is stirred with a water-immiscible solvent into which the diazoacetic acid ester is extracted. Alkali metal nitrites which may be used are, for example, the potassium or sodium salts, and the reaction with the glycine ester is preferably carried out in the presence of an acid catalyst, for example, sulphuric acid.

The solution of diazoacetic acid ester thus formed is then added to a solution of the diene of formula (II) maintained at the desired temperature, and containing the catalyst, usually in solution.

It is usual to use excess diene, the ratio of diene to diazoacetic ester being in the range 1:2 to 10:1.

Progress of the reaction may be monitored by measuring nitrogen evolution, which may also be used to determine yield of total products, the proportion of the desired product being readily determined by gas liquid chromatography (g.l.c.).

Separation of the desired product from the reaction mixture may be achieved by any convenient means; but it is generally convenient to first distil off the solvent, the diene then any esters of maleic and fumaric acids and finally the required product. Alternatively, the crude product, where it is a lower alkyl ester, after removal of solvent and unreacted diene may be used as an intermediate without further purification.

The reaction may also be performed continuously by forming the diazoacetic ester in a first vessel and continuously transferring it, in a solvent, to a second vessel where it is reacted immediately with the diene, as described and claimed in our British Pat. No. 1,459,285.

The starting material of formula (II) in which X and Y are each chlorine may be obtained, for example, by the condensation of 3-methylbut-1-ene with carbon tetrachloride in the presence of a free radical catalyst, followed by base-induced dehydrohalogenation of the 1,1,1,3-tetrahalo-4-methylpentane resulting from the condensation, a process which is fully described in United States Patent Specification No. 4,070,404.

Compounds of formula (II) in which one of X and Y represents a group of the formula Q—(CF$_2$)$_m$— as hereinbefore defined, and the other of X and Y represents fluorine, chlorine or bromine or a group

as hereinbefore defined, may be obtained, for example, by reacting a ketone of formula:

with 3-methylbut-1-ene, preferably under pressure, to give a compound of formula:

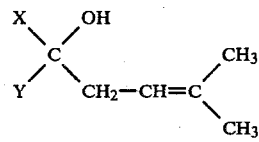

which may be dehydrated, with for example phosphorous pentoxide, to give the compound of formula:

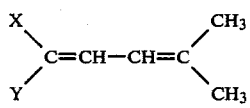

The compounds of formula (II) in which X and Y are both haloalkyl groups or wherein one of X and Y is a haloalkyl group and the other is a methyl group may be obtained, for example, by reacting a ketone of formula:

with the yield obtained by treating a 3,3-dimethylallyl-triphenylphosphonium halide, preferably the chloride or bromide, with a suitable dehydrohalogenating agent, for example, an alkyllithium compound such as n-butyllithium. The phosphonium halide may be obtained by reacting triphenylphosphine with a 3,3-dimethylallyl halide. Dienes of formula (II) which may be obtained by the process include those wherein X and Y are as defined in the following table:

| X | Y |
|---|---|
| CF$_3$ | CF$_3$ |
| CHF$_2$ | CHF$_2$ |
| CF$_3$ | CHF$_2$ |
| CF$_3$ | CH$_3$ |
| CF$_2$Cl | CF$_2$Cl |
| CHF$_2$ | CF$_2$Cl |

These processes are more fully described in our German Offenlegungsschrift No. 2802962.

Compounds of formula (I) in which R$^3$ is b 3-phenoxybenzyl, α-cyano-3-phenoxybenzyl or α-ethynyl-3-phenoxybenzyl, i.e. compounds having the formula:

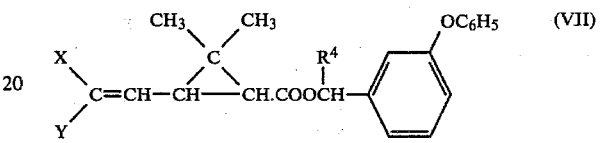

in which R$^4$ is H, CN or —C≡CH, are, in certain isomeric configurations, powerful insecticides, as disclosed in, for example, Belgian Patent Specification No. 863151 already referred to.

Compounds having the above formula (I) in which R$^3$ is lower alkyl may be converted by conventional methods of organic chemistry into the corresponding insecticidal 3-phenoxybenzyl, α-cyano-3-phenoxybenzyl or α-ethynyl-3-phenoxybenzyl esters. Thus, the compound of formula (I) in which R$^3$ is lower alkyl may be reacted with m-phenoxybenzyl alcohol or its α-cyano or α-ethynyl derivative in the presence of a transesterification catalyst such as sodium methoxide or ethoxide, or a titanium catalyst such as tetramethyl or tetraethyl titanate, to give the compound of formula (I) in which R$^3$ is 3-phenoxybenzyl, α-cyano-3-phenoxybenzyl or α-ethynyl-3-phenoxybenzyl. Alternatively, the compound of formula (I) in which R$^3$ is a lower alkyl group may be hydrolysed to give the corresponding free carboxylic acid [(I), R$^3$=H], which may then be converted into the acid chloride which is subsequently reacted with m-phenoxybenzyl alcohol or a derivative thereof.

The insecticidal compounds of formula (VII) are capable of existing in various geometrical and stereoisomeric forms. Thus, there are cis and trans isomers arising from the substitution pattern of the cyclopropane ring, and in particular the carbon atom at the 1-position bearing the carboxylic acid ester group may have either the R or S configuration. Consequently when R$^4$=H there are four isomeric possibilities for a compound of formula (VII) arising from the cyclopropane ring substitution, and these may be identified as cis-IR, trans-IR, cis-IS and trans-IS. In terms of insecticidal activity, the compounds having the cis-IR configuration are particularly potent and have substantially higher activity than the compounds having the trans-IR configuration. The corresponding compounds having the IS configuration are essentially insecticidally inactive. By cis we mean that the hydrogen atoms at carbon atoms 1 and 3 of the cyclopropane ring are in cis relationship to one another, and by trans we mean that the said hydrogen atoms are in trans relationship to one another.

In order to achieve the highest level of insecticidal activity it is desirable that compounds of formula (VII)

should have the maximum possible content of IR isomers and especially of the cis-IR isomer. The conversion of compounds of formula (I) into compounds of formula (VII) may be carried out without substantial alteration in the proportions of the various isomers, and consequently it is also desirable to obtain compounds of formula (I) having the maximum possible content of IR isomer.

Throughout this specification the term "aromatic system" means an essentially planar cyclic conjugated system containing $(4z+2)\pi$-electrons, z being a positive integer.

It is found that the process of the present invention provides compounds of formula (I) which are rich in the preferred cis-IR isomer.

Consequently the derived insecticides of formula (VII) will also be rich in cis-IR isomer and have high activity. Furhermore the yield of compound of formula (I) prepared according to the process of the present invention is in general higher than the corresponding yield under similar conditions from a diene of formula $R^1R^2C=CH-CH=C(CH_3)_2$ and a lower alkyl ester of diazoacetic acid as described in Belgian Patent Specification No. 863151 already referred to. Formation of the cis-IR isomer is often favoured by the use of chiral metal complex catalysts of classes (i) to (iii) as hereinbefore defined, and surprisingly, this is particularly so when the chiral catalysts have the S configuration which is generally the configuration of naturally occurring amino-acids and monosaccharides, thus making such catalysts readily accessible.

With regard to the catalysts of class (i) derived from a chiral Schiff base having the general formula (IV), specific examples of the chain J are

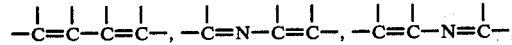

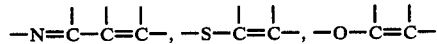

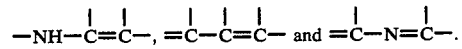

Examples of substituents $R^8$ and $R^9$ in general formula (IV) are methyl, ethyl, n-propyl, isopropyl, n-butyl, isobutyl, sec-butyl, tert-butyl, octyl, cyclohexyl, cyclohexylmethyl, benzyl, benzhydryl, 2,2-diphenylethyl, phenyl, tolyl and naphthyl.

Specific examples of L when it represents a substituent containing at least one hetero atom are OH, $OR^{23}$, $OCOR^{23}$, CHO, $COR^{23}$, $CO_2H$, $CO_2R^{23}$, CN, $CONH_2$, $NH_2$, $NHR^{23}$, $NR^{23}_2$, $NHCOR^{23}$, $NO_2$, SH, $SR^{23}$, $SOR^{23}$, $SO_3R^{23}$, $SO_3H$ or a halogen atom. $R^{23}$ in the above substituents is alkyl, aralkyl or aryl.

Preferred chiral Schiff bases of formula (IV) are those in which $R^8$ is a substituted phenyl group, $R^{10}$ is hydrogen, J is

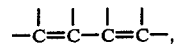

K is nitrogen, L is hydrogen, m is 4 and n is 0 (i.e. the cyclic nucleus in general formula (IV) is a pyridine nucleus). It is also preferred that $R^8$ represents a phenyl group having a substituent at the 2-position or having substituents at the 2,5- or 2,6-positions.

Examples of the substituted phenyl groups represented by $R^8$ are 2-methoxyphenyl, 2-ethoxyphenyl, 2-propoxyphenyl, 2-isopropoxyphenyl, 2-butoxyphenyl, 2-tert-butoxyphenyl, 2-octyloxyphenyl, 2-benzyloxyphenyl, 2-phenoxyphenyl, 2-methoxy-5-methylphenyl, 2-butoxy-5-methylphenyl, 2-benzyloxy-5-methylphenyl, 5-tert-butyl-2-methoxyphenyl, 2-butoxy-5-tert-butylphenyl, 5-tert-butyl-2-octyloxyphenyl, 2-benzyloxy-5-tert-butylphenyl, 4-methoxybiphenyl-3-yl, 2,5-dimethoxyphenyl, 2,5-dibutoxyphenyl, 2,5-dioctyloxyphenyl and 2,5-dibenzyloxyphenyl.

The novel chiral Schiff bases, the metal complexes of which form the catalysts of class (i) above, may be obtained by reacting a chiral amino alcohol having the formula:

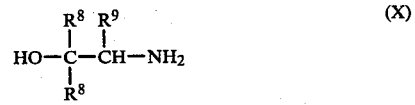

with a carbonyl compound having the formula:

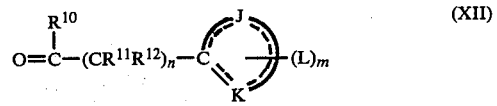

wherein $R^8$, $R^9$, $R^{10}$, $R^{11}$, $R^{12}$, J, K, L, m and n have the previously defined meanings.

The reaction is preferably carried out in the presence of an inert solvent in which the Schiff base is insoluble and is effected near the reflux temperature of the solvent.

Suitable solvents include aromatic hydrocarbons, e.g. toluene, alcohols, e.g. methanol, and halogenated hydrocarbons, e.g. 1,2-dichloroethane and chloroform.

Examples of specific compounds of formula (XII) which may be used to prepare the novel Schiff bases are pyridine-2-carboxaldehyde, 2-acetylpyridine, pyridoxal, quinoline-8-carboxaldehyde, 8-acetylquinoline, pyridine-2-carboxaldehyde-N-oxide and pyrrole-2-carboxaldehyde.

Whilst the chiral amino alcohol of formula (X) may be obtained by optical resolution of a mixture of enantiomers, preferably it is prepared from a chiral starting material. $\alpha$-Aminoacid esters are convenient starting materials and they may be converted into suitable chiral aminoalcohols by known methods using appropriate Grignard reagents.

An example of an amino-alcohol of formula (X) is 2-amino-1,1-di(2-methoxyphenyl)-3-phenylpropan-1-ol.

The compounds of formula (IV) in which K is $N \rightarrow O$ may be obtained by oxidation of the corresponding compounds in which K is unsubstituted nitrogen. A suitable oxidising agent for this purpose is hydrogen peroxide.

The catalysts of Class (i) in which a transition metal is coordinated with a chiral Schiff base have the general formulae:

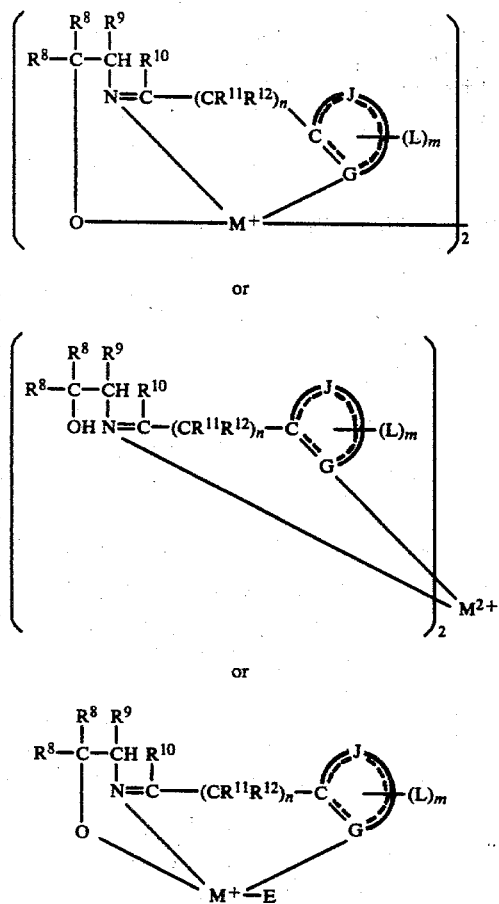

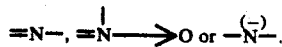

in which $R^8$, $R^9$, $R^{10}$, $R^{11}$, $R^{12}$, J, L, m and n have the previously defined meanings, E is a monodentate neutral ligand, M is a metal from the first or second series of the main group of transition metals and G is $$=N-, \quad =N\longrightarrow O \text{ or } -\overset{(-)}{N}-.$$

By transition metal we mean a metal which, in any one of its commonly occurring oxidation states, has only a partly filled d shell. In the first transition metal series the partly filled d shell is 3d. In the second series the partly filled d shell is 4d.

Preferably the metal is copper(II), chromium(II), nickel(II), manganese(II), iron(II), iron(III), cobalt(II) or palladium(II). Particularly preferably the metal is copper(II).

Examples of ligand E in general formula (XIVA) include Lewis bases, such as amines, e.g. pyridine, and tertiary phosphine oxides.

It will be appreciated that complexes according to the general formula (XIII) above are bi-nuclear and complexes according to the general formulae (XIV) and (XIVA) are mono-nuclear, and that in the complexes according to the general formulae (XIII) and (XIVA) the Schiff base behaves as a tridentate ligand and that in complexes according to the general formula (XIV) the Schiff base behaves as a bidentate ligand.

A preferred group of metal complexes for use as catalysts according to the present invention are those of general formula (XIV) since these give a higher optical yield than that given by the metal complexes of general formulae (XIII) or (XIVA).

In the catalysts of general formulae (XIII), (XIV) or (XIVA) it is preferred that $R^8$ is a substituted phenyl group, $R^{10}$ is hydrogen, J is

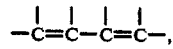

G is nitrogen, L is hydrogen and n is O.

It will be appreciated that in chiral metal complexes as defined in formulae (XIII), (XIV) and (XIVA) where G is =N— or

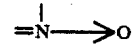

the metal carries a positive charge and that an anion is necessary to provide an ionically neutral compound. The anions associated with the metal complexes may be inorganic or organic, provided that they are derived from strong acids having a pKa value less than 2.5.

The anions should not be oxidising or reducing agents or otherwise chemically reactive with diazoacetic esters or other materials used in the process according to the present invention. Suitable anions include, inter alia, halide, tetrafluoroborate, methosulphate, sulphate, bisulphate, aromatic sulphonate, fluorosilicate and tetraphenylborate.

Various methods are available for preparing the metal complexes of chiral Schiff bases as hereinbefore defined. The Schiff base may be reacted with a suitable salt of the appropriate metal. The aminoalcohol may be reacted with an appropriate metal ketone or aldehyde complex, e.g. bis(salicylaldehydato)copper(II). The preferred method involves reacting the Schiff base with an appropriate metal ketone or aldehyde complex; the metal complexes obtained by this method tend to be more selective than those obtained by other methods.

Catalysts of class (i) and their preparation are the subject of a co-pending United Kingdom Patent Application.

With regard to the catalysts of class (ii) derived from a chiral Schiff base having the general formula (V), Specific examples of the conjugated chain $J^1$ are

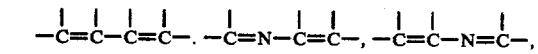

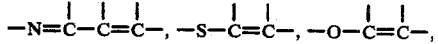

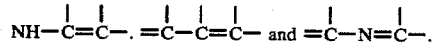

Specific examples of the substituent $L^1$ containing (a) heteroatom(s) are OH, $OR^{24}$, $-CO_2H$, $CO_2R^{24}$, CN, $CONH_2$, $NH_2$, $NHR^{24}$, $NR_2^{24}$, $NHCOR^{24}$, $NO_2$, SH, $SR^{24}$, $SOR^{24}$, $SO_3H$, $SO_3R^{24}$ or halogen. $R^{24}$ in the above substituents is alkyl, aralkyl or aryl.

It will be appreciated that the monosaccharide portion of the novel chiral Schiff bases which, in general formula (V), are shown in the cyclic hemiacetal or hemiketal form, may exist in equilibrium with the corresponding open chain form having a free carbonyl group. Moreover, while the monosaccharide may exist in the furanose form (5-membered ring), the pyranose form is usually more stable for the free monosaccharide.

Preferably r is O, q is 1, $R^{13}$, $R^{14}$ and $R^{16}$ are hydrogen, $R^1$ is —$CH_2OR^{22}$, $R^{17}$ is lower alkyl, e.g. methyl, $L^1$ is hydrogen and (a) $J^1$ is

and $K^1$ is nitrogen or

i.e. the aromatic system in general formula (V) is pyrid-2-yl or 2-hydroxyphenyl, or (b) $J^1$ is

and $K^1$ is —NH—, i.e. the aromatic system in general formula (V) is pyrrol-2-yl.

Particularly preferably p is O, $R^{21}$ is hydrogen, $J^1$ is

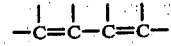

$L^1$ is hydrogen, s is 4 and $K^1$ is nitrogen or COH.

More particularly preferably chiral Schiff bases the transition metal complexes of which may be used in the process of the present invention have the general structure represented by the modified Haworth projection formula:

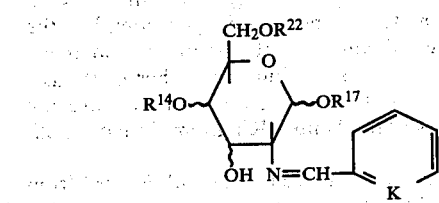

where $R^{17}$ is lower alkyl, $R^{14}$ and $R^{22}$ are both hydrogen or together form a divalent hydrocarbon group and K is nitrogen or COH; since we have found that these chiral Schiff bases in which the pyranose ring has the configuration at C2 (the carbon bonded to the carbon of the acetal or hemiacetal group) specified in general formula (V) form metal complexes which, when employed as catalysts in the process according to the present invention often give preferentially cyclopropane carboxylic acid esters having the 1R configuration.

Examples of specific amino-monosaccharides from which, or from derivatives of which, novel chiral Schiff bases of formula(XV) may be prepared, include inter alia 2-amino-2-deoxy-D-glucose, 2-amino-2-deoxy-D-allose, 2-amino-2-deoxy-D-galactose, 2-amino-2-deoxy-D-altrose,
2-amino-2-deoxy-D-mannose, 2-amino-2-deoxy-D-ribose and
2-amino-2-deoxy-D-xylose.

Examples of specific carbonyl compounds from which novel chiral Schiff bases of formula (XV) may be prepared include inter alia salicylaldehyde, 2-hydroxy-1-naphthaldehyde, pyridine-2-carboxaldehyde, pyridine-2-carboxaldehyde-N-oxide, 2-acetylpyridine, quinoline-8-carboxaldehyde, pyridoxal and pyrrole-2-carboxaldehyde.

The catalysts of class (ii) in which a transition metal is coordinated with a chiral Schiff base of formula (XV) have the general formula:

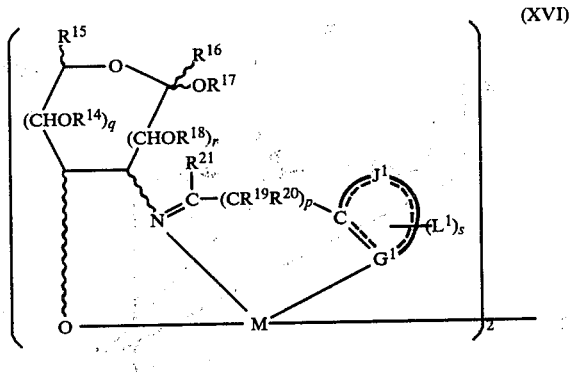

or

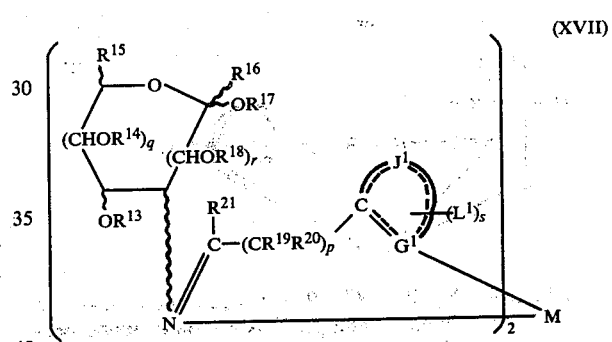

or

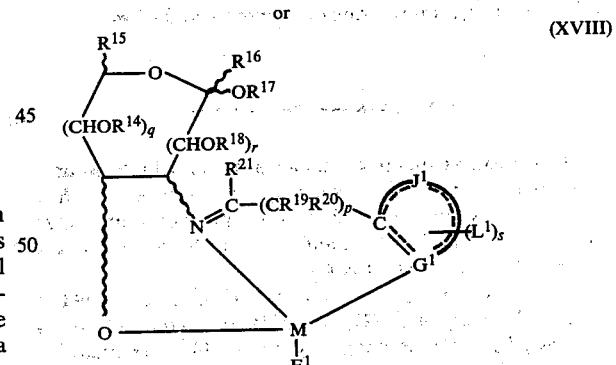

wherein
$R^{13}$, $R^{14}$ and $R^{18}$ which may be the same or different, are hydrogen or lower alkyl, except that at least one of $R^{13}$ and $R^{18}$ is hydrogen;
$R^{15}$ is hydrogen, a sugar derivative or —$CH_2OR^{22}$, in which $R^{22}$ is hydrogen, lower alkyl or together with $R^{14}$ forms a divalent hydrocarbon group;
$R^{16}$ is hydrogen or —$CH_2OR^{22}$ in which $R^{22}$ is hydrogen or lower alkyl;
$R^{17}$ is hydrogen, lower alkyl or a sugar derivative;
$R^{19}$ and $R^{20}$, which may be the same or different, are hydrogen or lower alkyl, or where p is 1, may with the cyclic ring to which $CR^{19}R^{20}$ is attached form a fused ring system;

$R^{21}$ is hydrogen, alkyl, aralkyl or aryl;

$E^1$ is a monodentate neutral ligand;

$G^1$ is nitrogen,

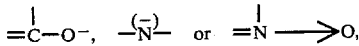

$J^1$ is a chain of 3 or 4 atoms consisting either exclusively of carbon atoms or carbon atoms together with one or more hetero atoms which may be the same or different, which chain with the group $-C\quad G^1-$ forms an aromatic system $L^1$, each of which may be the same or different, represents a substituent attached to a carbon atom in the chain $J^1$ and is hydrogen, alkyl, aralkyl, aryl or a substituent containing a hetero-atom, or two groups $L^1$ together with the ring to which they are attached form a fused ring system;

M is a metal from the first or second series of the main group of transition metals;

r is 0 or 1;

q is 0, 1 or 2 provided that q+r are 1, 2 or 3;

p is 0, 1 or 2 and s is the number of carbon atoms in the chain $J^1$.

In the above definition the term "lower alkyl" means an alkyl group having 1 to 4 carbon atoms.

By transition metal we mean a metal which, in any one of its commonly occurring oxidation states, has a partly filled d shell only. In the first series the partly filled d shell is 3d and in the second series the partly filled d shell is 4d.

Preferably the metal is copper(II), chromium(II), manganese(II), iron(II) and (III), cobalt(II), nickel(II) or palladium(II). Particularly preferably the metal is copper(II).

It will be appreciated that complexes according to the general formula (XVI) are bi-nuclear and complexes according to the general formulae (XVII) and (XVIII) are mononuclear; and that in the complexes according to the general formulae (XVI) and (XVIII) the Schiff base behaves as a tridentate ligand and that in complexes according to the general formula (XVII) the Schiff base behaves as a bidentate ligand.

Ligands $E^1$ are suitably Lewis bases, examples are tertiary phosphine oxides and amines such as pyridine.

A preferred group of metal complexes for use in the invention are those according to general formula (XVII) given above since they give a higher enantiomer excess in the reaction of a diene of formula (II) with a diazoacetate than given by the metal complexes according to general formulae (XVI) and (XVIII).

In metal complexes according to the general formulae (XVI), (XVII) or (XVIII), preferably r is 0 and q is 1, $R^{14}$ and $R^{16}$ are hydrogen, $R^{15}$ is $CH_2OR^{22}$, $R^{17}$ is lower alkyl, e.g. methyl, $L^1$ is hydrogen and $J^1$ is

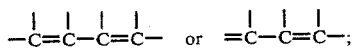

particularly preferably p is 0, $R^{21}$ is hydrogen, $J^1$ is

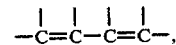

$L^1$ is hydrogen, s is 4 and $G^1$ is nitrogen or

more particularly preferably the metal complex has the general structure represented by the modified Howarth projection formulae:

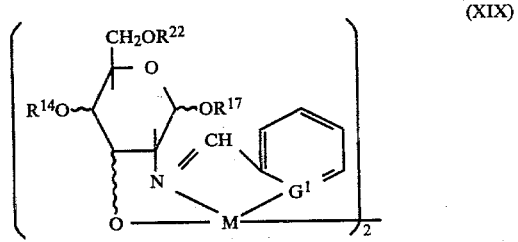
(XIX)

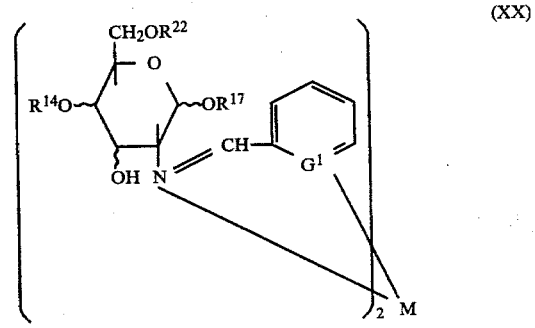
(XX)

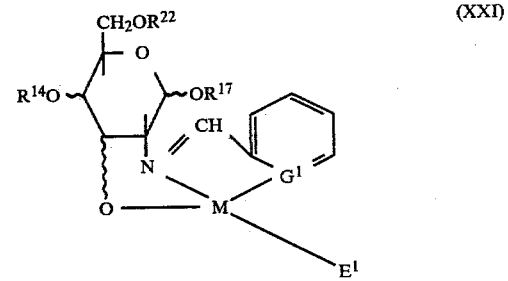
(XXI)

where $R^{17}$ is lower alkyl, e.g. methyl, $R^{14}$ and $R^{22}$ are hydrogen, or together form a divalent hydrocarbon radical, $G^1$ is nitrogen or

and $E^1$ has the previously defined meaning.

Where, in the general formulae (XVI)-(XXI), $G^1$ is nitrogen or NO, the metal complex carries a positive charge and an anion is necessary to provide an electrically neutral compound. The anions associated with the metal cation may be inorganic or organic, provided that they are derived from strong acids having a pKa value less than 2.5.

The anions should not be oxidising or reducing agents or otherwise chemically reactive with diazoacetic esters or other materials used in the process according to the present invention. Suitable anions include, inter alia, halide, tetrafluoroborate, methosulphate, bisulphate, sulphate, aromatic sulphonate, fluorosilicate and tetraphenylborate.

Amino-sugars useful for the preparation of chiral Schiff bases, the transition metal complexes of which may be used in the process of the present invention, may be naturally occurring, e.g. D-glucosamine or D-mannosamine, or they may be prepared from monosaccharides or from naturally occurring aminomonosaccharides.

The chiral Schiff bases of class (ii) may be obtained by reacting the appropriate amino-sugar with a carbonyl compound having the formula:

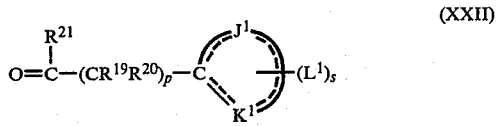
(XXII)

wherein $R^{19}$, $R^{20}$, $R^{21}$, $J^1$, $K^1$, $L^1$, p and s have the previously defined meanings.

The reaction is preferably carried out in the presence of an inert solvent. Suitable solvents include aromatic hydrocarbons, e.g. toluene; alcohols, e.g. methanol, and halogenated hydrocarbons, e.g. 1,2-dichloroethane and chloroform.

Various methods are available for preparing the metal complexes of chiral Schiff bases of class (ii). The Schiff base may be reacted with a suitable salt of the appropriate metal. The amino-monosaccharide may be reacted with an appropriate metal keto or aldehyde complex, e.g. bis(salicylaldehydato)copper(II). The preferred method involves reacting the Schiff base with an appropriate metal-keto or metal-aldehyde complex; the metal complexes obtained by this method tend to be more selective than those obtained by other methods.

Catalysts of class (ii) and their preparation are the subject of a co-pending United Kingdom Patent Application.

With regard to catalysts of class (iii) derived from a chiral Schiff base having the general formula (VA), examples of alkyl groups represented by $R^{25}$, $R^{26}$, $R^{27}$ and $R^{30}$ are methyl, ethyl, n-propyl, iso-propyl, n-butyl, iso-butyl, sec-butyl, tert-butyl, n-pentyl, n-hexyl, cyclohexyl, n-octyl, 2-ethylhexyl, n-decyl and n-dodecyl. Where $R^{25}$, $R^{26}$ or $R^{27}$ include one or more hetero atoms, specific examples include OH, $OR^{33}$, $OCOR^{33}$, CHO, $COR^{33}$, $CO_3H$, $CO_2R^{33}$, CN, $CONH_2$, $NH_2$, $NHR^{33}$, $NR_2^{33}$, $NHCOR^{33}$, $NO_2$, SH, $SOR^{33}$, $SO_3H$, $SO_3R^{33}$ or a halogen atom. $R^{33}$ in the above substituents is alkyl, aralkyl or aryl.

Examples of aralkyl groups represented by $R^{30}$ are benzyl and 2-phenylethyl.

Examples of substituents $R^{31}$ and $R^{32}$ in general formula (VB) are methyl, ethyl, propyl, iso-propyl, butyl, iso-butyl, sec-butyl, tert-butyl, octyl, cyclohexyl, cyclohexylmethyl, benzyl, benzhydryl, 2,2-diphenylethyl, phenyl, tolyl and naphthyl. In compounds of formula (VA) containing groups $J^2$ and $K^2$ represented by formula (VB), preferably $R^{25}$, $R^{26}$, $R^{27}$ and $R^{30}$ are hydrogen, $R^{32}$ is a substituted phenyl group and n is 0.

It is also preferred that $R^{32}$ represents a phenyl group having a substituent at the 2-position or substituents at the 2,5- and 2,6-positions. Examples of such substituted phenyl groups are those given for the group $R^8$ in catalyst class (i) above.

It will be appreciated that the monosaccharide substituents represented by $J^2$ and $K^2$ which, in formula (VC), are shown in the cyclic hemiacetal or hemiketal form may exist in equilibrium with the corresponding open-chain form having a carbonyl group. Moreover, while the monosaccharide may exist in the furanose form (five membered ring) the pyranose form is usually more stable for the free monosaccharide.

Where groups $J^2$ and $K^2$ are represented by formula (VC) preferably r=0, q=1, $R^{13}$, $R^{14}$ and $R^{16}$ are hydrogen, $R^{15}$ is $-CH_2OR^{22}$, $R^{17}$ is lower alkyl, e.g. methyl and particularly preferably $J^2$ and $K^2$ have the general structure represented by the modified Howarth projection formula:

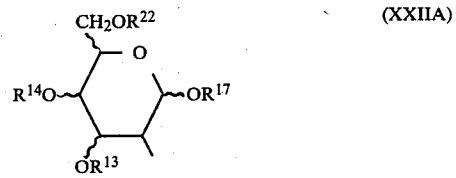
(XXIIA)

wherein $R^{17}$ is lower alkyl, $R^{13}$ is hydrogen and $R^{14}$ and $R^{22}$ are both hydrogen or together form a divalent hydrocarbon group, since it has been found that these chiral Schiff bases in the pyranose ring has the configuration at C2 (the carbon bonded to the carbon of the acetal or hemiacetal group) specified in general formula (XXIIA) form metal complexes which, when employed as catalysts in the process according to the present invention often give preferentially cyclopropane carboxylic acid esters having the IR configuration.

The chiral Schiff bases, the metal complexes of which form the catalysts of class (iii) above, may be obtained by reacting an amino monosaccharide having the formula:

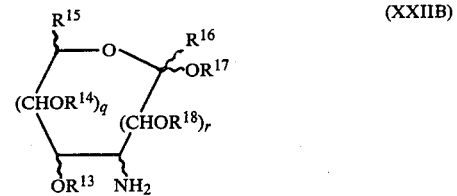
(XXIIB)

or a chiral amino alcohol having the formula:

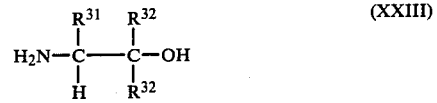
(XXIII)

with a dicarbonyl compound having the formula

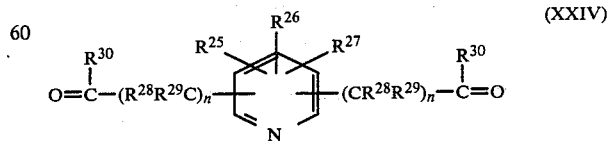
(XXIV)

wherein $R^{13}$, $R^{14}$, $R^{15}$, $R^{16}$, $R^{17}$, $R^{18}$, $R^{25}$, $R^{26}$, $R^{27}$, $R^{28}$, $R^{29}$, $R^{30}$, $R^{31}$, $R^{32}$ and n, q and r have the previously defined meanings.

The reaction is preferably carried out in the presence of an inert solvent in which the Schiff base is insoluble and is effected near the reflux temperature of the solvent.

Suitable solvents include aromatic hydrocarbons, e.g. toluene; alcohols, e.g. methanol, and halogenated hydrocarbons, e.g. 1,2-dichloroethane and chloroform.

Examples of specific compounds of formula (XXIV) which may be used to prepare the Schiff bases of formula (VA) are pyridine-2,6-dicarboxaldehyde and 2,6-diacetylpyridine.

Whilst the chiral amino alcohol of formula (XXIII) may be obtained by optical resolution of a mixture of enantiomers, preferably it is prepared from a chiral starting material. α-Amino acid esters are convenient starting materials and they may be converted into suitable chiral aminoalcohols by known methods using appropriate Grignard reagents. An example of an aminoalcohol of formula (XXIII) is 2-amino-1,1-di(2-methoxyphenyl)-3-phenylpropan-1-ol.

The compounds of formula (VA) having an oxygen atom on the ring nitrogen may be obtained by oxidation of the corresponding compounds of formula (VA) in which the ring nitrogen is unsubstituted. A suitable oxidising agent for this purpose is hydrogen peroxide.

The catalysts of class (iii) in which a transition metal is coordinated with a chiral Schiff base are believed to have structures represented by the general formula:

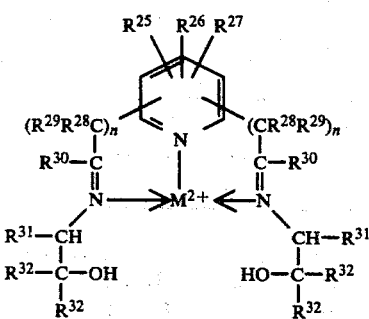

(XXV)

wherein $R^{25}$, $R^{26}$, $R^{27}$, $R^{28}$, $R^{29}$, $R^{30}$, $R^{31}$, $R^{32}$ and n have the previously defined meanings and M is a metal from the first or second series of the main group of transition metals, as defined in connection with catalysts of class (i).

Preferably the metal is copper(II), chromium(II), manganese(II), iron(II), iron(III), cobalt(II), nickel(II) or palladium(II). Particularly preferably the metal is copper(II). It will be appreciated that in chiral metal complexes as defined in formula (XXV) the metal carries a positive charge and that an anion is necessary to provide an ionically neutral compound. The anions associated with the metal complexes may be inorganic or organic provided that they are derived from strong acids having a pKa value less than 2.5.

The anions should not be oxidising or reducing agents or otherwise chemically reactive with diazoacetic esters or other materials used in the process according to the invention. Suitable anions include, inter alia; halide, tetrafluoroborate, methosulphate, bisulphate, sulphate, aromatic sulphonate, fluorosilicate and tetraphenylborate.

Various methods are available for preparing the metal complexes of the chiral Schiff bases of formula (VA). The Schiff base may be reacted with a suitable salt of the appropriate metal. The aminoalcohol of formula (XXIII) may be reacted with an appropriate metal complex of an aldehyde or ketone of formula (XXIV); or the Schiff base may be reacted with an appropriate metal ketone or aldehyde complex; the metal complexes obtained by this latter method tend to be more selective than those obtained by other methods.

Catalysts of class (iii) and their preparation are the subject of a copending United Kingdom Patent Application.

The preparation of typical chiral Schiff bases, and of metal complexes of chiral Schiff bases of class (ii) for use according to the process of the present invention, is described below:

A. Preparation of methyl N-salicylidene-4,6-O-benzylidene-2-amino-2-deoxy-α-D-altropyranoside. Methyl 4,6-O-benzylidene-2-amino-2-deoxy-α-D-altropyranoside (0.7 g.) (prepared by the method of W. H. Meyer and G. H. Robertson, J. Amer. Chem. Soc. 1943, 65, 8) and salicylaldehyde (0.3 g.) in toluene (50 ml.) were refluxed for 2 hours. The reaction mixture was cooled and the precipitate was filtered off. Recrystallisation from methanol/petroleum ether (b.p. 40°-60° C.) gave methyl N-salicylidene-4,6-O-benzylidene-2-amino 2-deoxy-α-D-altropyranoside (m.p. 218° C.).

| Elemental analysis for $C_{21}H_{23}O_6N$ | | | |
|---|---|---|---|
| | C | H | N |
| Found: | 65.38 | 5.82 | 3.28 |
| Calculated | 65.45 | 5.97 | 3.60 |

B. By similar procedure to that described in A above, other chiral Schiff bases were prepared from methyl 4,6-O-benzylidene-2-amino-2-deoxy-α-D-altropyranoside and the appropriate carbonyl compounds as follows:

(a) Methyl N-(2-hydroxynaphthylidene)-4,6-O-benzylidene-2-amino-2-deoxy-α-D-altropyranoside (m.pt. 243° C.) was prepared from 2-hydroxynaphth-1-aldehyde.

| Elemental analysis for $C_{25}H_{25}O_6N$ | | | |
|---|---|---|---|
| | C | H | N |
| Found: | 68.00 | 5.96 | 2.79 |
| Calculated | 68.97 | 5.75 | 3.22 |

(b) Methyl N-(2-pyridinylidene)-4,6-O-benzylidene-2-amino-2-deoxy-α-D-altropyranoside was prepared from pyridine-2-carboxaldehyde.

| Elemental analysis for $C_{20}H_{22}N_2O_5$ | | | |
|---|---|---|---|
| | C | H | N |
| Found: | 63.82 | 6.07 | 6.96 |
| Calculated | 64.86 | 5.95 | 7.57 |

C. Preparation of chiral Schiff bases from methyl 4,6-O-benzylidene-2-amino-2-deoxy-β-D-altropyranoside (prepared by the method of W. H. Mayer and G. J. Robertson, J. Amer. Chem. Soc. 1943, 65, 8).

(a) The amino-monosaccharide (0.45 g.) and salicylaldehyde (0.2 g.) were refluxed in ethanol (30 ml.) for 2 hours. The solvent was evaporated off and the residual methyl N-salicylidene-4,6-O-benzylidene- 2-amino-2-deoxy-β-D-altropyranoside had a m.pt. of 190°–200° C.

(b) The amino-monosaccharide (0.4 g.) and 2-hydroxynaphth-1-aldehyde (0.25 g.) were refluxed in ethanol (20 ml.) for 2 hours. The solvent was evaporated off and the residual methyl N-(2-hydroxynaphthylidene)-4,6-O-benzylidene-2-amino-2-deoxy-β-D-altropyranoside had a m.pt. of 115° C.

(c) The amino-monosaccharide (0.5 g.) and pyridine-2-carboxaldehyde (0.2 g.) were refluxed in methanol (20 ml.) for 2 hours. The solvent was evaporated off and the residual methyl N-(2-pyridinylidene)-4,6-O-benzylidene-2-amino-2-deoxy-β-D-altropyranoside had a m.pt. of 248° C.

D. Preparation of chiral Schiff bases from methyl 4,6-O-benzylidene-2-amino-2-deoxy-α-D-allopyranoside (prepared by the method of C. B. Barlow and E. A. Guthrie *J. Chem. Soc. (Part C)* 1967, 1196).

(a) The amino-monosaccharide (1.48 g.) and salicylaldehyde (0.74 g.) were refluxed in toluene (40 ml.) for 2½ hours. The solvent was evaporated off at reduced pressure and the residue crystallised to give methyl N-salicylidene-4,6-O-benzylidene-2-amino-2-deoxy-α-D-allopyranoside (1.38 g; m.pt. 188°–192° C.).

| Elemental analysis for $C_{21}H_{23}NO_6$ | | | |
|---|---|---|---|
| | C | H | N |
| Found: | 64.08 | 6.19 | 3.14 |
| Calculated | 65.45 | 5.97 | 3.64 |

(b) The amino-monosaccharide (0.70 g.) and pyridine-2-carboxaldehyde (0.27 g.) were refluxed in toluene (20 ml.) for 2½ hours. The solvent was evaporated off at reduced pressure and the residue was dried in vacuo to give methyl N-(2-pyridinylidene)-4,6-O-benzylidene-2-amino-2-deoxy-α-D-allopyranoside as a golden solid (0.68 g; m.pt. 54°–60° C.).

| Elemental analysis for $C_{20}H_{22}N_2O_5$ | | | |
|---|---|---|---|
| | C | H | N |
| Found: | 62.96 | 6.43 | 6.76 |
| Calculated | 64.86 | 5.94 | 7.57 |

E. Preparation of chiral Schiff bases from methyl 2-amino-2-deoxy-β-D-glucopyranoside (prepared by the method of A. Neuberger and R. P. Rivers, *J. Chem. Soc.* 1939, 122).

(a) The amino-monosaccharide (0.8 g.) and salicylaldehyde (0.55 g.) were heated at reflux in ethanol (50 ml.) for 2 hours. The reaction mixture was evaporated to dryness to leave methyl N-salicylidene-2-amino-2-deoxy-β-D-glucopyranoside as a yellow oil.

(b) The amino-monosaccharide (0.8 g.) and 2-hydroxy-1-naphthaldehyde were heated at reflux in ethanol (50 ml.) for 2 hours. The reaction mixture was evaporated to dryness to leave methyl N-(2-hydroxy-1-naphthylidene)-2-amino-2-deoxy-β-D-glucopyranoside as a green oil.

(c) The amino-monosaccharide (0.8 g.) and pyridine-2-carboxaldehyde (0.44 g.) were heated at reflux in ethanol (50 ml.) for 2 hours. The reaction mixture was evaporated to dryness to leave methyl N-(2-pyridinylidene)-2-amino-2-deoxy-β-D-glucopyranoside as a yellow solid.

F. Preparation of chiral Schiff bases from methyl 2-amino-2-deoxy-α-D-glucopyranoside (prepared by the method of A. Neuberger and R. P. Rivers, *J. Chem. Soc.* 1939, 122).

(a) The amino-monosaccharide (0.6 g.) and salicylaldehyde (0.38 g.) were heated at reflux in ethanol (50 ml.) for 2 hours. The reaction mixture was evaporated to dryness to leave methyl N-(salicylidene)-2-amino-2-deoxy-α-D-glucopyranoside as a yellow oil.

(b) The amino-monosaccharide (0.6 g.) and pyridine-2-carboxaldehyde (0.33 g.) were heated at reflux in ethanol (50 ml.) for 2 hours. The reaction mixture was evaporated to dryness to leave methyl N-(2-pyridinylidene)-2-amino-2-deoxy-α-D-glucopyranoside as a yellow oil.

G. Preparation of metal complexes of Schiff bases of methyl 4,6-O-benzylidene-2-amino-2-deoxy-α-D-altropyranoside.

(a) Methyl N-(2-hydroxynaphthylidene)-4,6-O-benzylidene-2-amino-2-deoxy-α-D-altropyranoside (0.435 g.) was added in portions over 1 hour with stirring to $Cu^{II}$bis(salicylaldehyde) (0.153 g.) (prepared by reacting cupric chloride and sodium salicylaldehyde in water, extracting into toluene and evaporating) in methanol (10 ml). The reaction mixture was stirred for 3 hours and the mononuclear copper complex of the Schiff base was filtered off, m.pt. 218° C., $[\alpha]D = +35°$.

| Elemental Analysis for $C_{50}H_{50}O_{12}N_2Cu$ | | | |
|---|---|---|---|
| | C | H | N |
| Found: | 63.79 | 4.79 | 2.70 |
| Calculated | 64.27 | 5.36 | 3.00 |

(b) Methyl N-(2-hydroxynaphthylidene)-4,6-O-benzylidene-2-amino-2-deoxy-α-D-altropyranoside (0.453 g.) and cupric acetate·$H_2O$ (0.2 g.) were heated at reflux in methanol (20 ml.) for 30 minutes. The binuclear copper complex of the Schiff base was filtered off, dec. >250°, $[\alpha]_D = 200°$.

| Elemental analysis for $C_{25}H_{25}O_6NCu$ | | | |
|---|---|---|---|
| | C | H | N |
| Found: | 59.80 | 5.25 | 1.90 |
| Calculated | 60.18 | 5.02 | 2.81 |

(c) Cupric chloride·$2H_2O$ (0.170 g.) in water (4 ml.) was added slowly to methyl N-(2-pyridinylidene)-4,6-O-benzylidene-2-amino-2-deoxy-α-D-altropyranoside (1.23 g.). Water (2 ml.) and methanol (6 ml.) were added and the mixture was stirred for 30 minutes. Sodium fluoroborate (0.2 g.) in water (1 ml.) was added and stirring was continued for 10 minutes. The solvent was evaporated off to leave the mononuclear copper complex of methyl N-(2-pyridinylidene)-4,6-O-benzylidene-2-amino-2-deoxy-α-D-altropyranoside as a green residue m.pt. 170° C.

(d) Methyl N-salicylidene-4,6-O-benzylidene-2-amino-2-deoxy-α-D-altropyranoside (0.385 g.) was added in portions with stirring over 1 hour to $Cu^{II}$bis(salicylaldehyde) (0.153 g.) in methanol (10 ml.). The reaction mixture was stirred for 1 hour and a solid was filtered off. Evaporation of the filtrate left a mononuclear copper complex of methyl N-salicylidene-4,6-O-benzylidene-2-amino-2-deoxy-α-D-altropyranoside, m.pt. 190°–205° C. $[\alpha]_D = +300°$.

| Elemental analysis for $C_{42}H_{44}N_2O_{12}Cu$ | | | |
| --- | --- | --- | --- |
| | C | H | N |
| Found: | 62.90 | 5.33 | 2.81 |
| Calculated | 60.60 | 5.29 | 3.37 |

(e) Methyl 4,6-O-benzylidene-2-amino-2-deoxy-α-D-altropyranoside (0.56 g.) in methanol (10 ml.) was added dropwise with stirring to a suspension of $Cu^{II}$bis(salicylaldehyde) (0.154 g.) in methanol (5 ml.). The reaction mixture was stirred for 3 hours and then filtered.

(f) Methyl N-salicylidene-4,6-O-benzylidene-2-amino-2-deoxy-α-D-altropyranoside (0.385 g.) and cupric acetate .$H_2O$ (0.2 g.) were heated under reflux in methanol (10 ml.) for 10 minutes. The methanol was evaporated off and the residue was extracted with toluene. The toluene extract was washed with a saturated aqueous sodium bicarbonate solution, then with water, dried and the toluene evaporated off to leave a binuclear copper complex of methyl N-salicylidene-4,6-O-benzylidene-2-amino-2-deoxy-α-D-altropyranoside, m.pt. 188° C. $[\alpha]_D + 530°$.

| Elemental analysis for $C_{21}H_{21}NO_6Cu$ | | | |
| --- | --- | --- | --- |
| | C | H | N |
| Found: | 52.00 | 5.32 | 2.20 |
| Calculated | 56.30 | 4.92 | 3.13 |

H. Preparation of metal complexes of Schiff bases of methyl 4,6-O-benzylidene-2-amino-2-deoxy-β-D-altropyranoside.

(a) Methyl N-salicylidene-4,6-O-benzylidene-2-amino-2-deoxy-β-D-altropyranoside (0.35 g.) was added in portions over 1 hour with stirring to $Cu^{II}$bis(salicylaldehyde) (0.14 g.) (prepared as in G) in methanol (10 ml.) at 20° C. The reaction mixture was stirred for 2 hours and a solid was filtered off. The filtrate was evaporated to dryness to leave a copper complex of the Schiff base.

(b) Methyl N-(2-hydroxynaphthylidene)-4,6-O-benzylidene-2-amino-2-deoxy-β-D-altropyranoside (0.5 g.) and $Cu^{II}$bis(salicylaldehyde) were reacted as above to give a copper complex of the Schiff base.

(c) Cupric chloride 0.2$H_2O$ (0.069 g.) in water (2 ml.) was added slowly with stirring to methyl N-(2-pyridinylidene-4,6-O-benzylidene-2-amino-2-deoxy-β-D-altropyranoside (0.5 g.) in methanol (10 ml.). The reaction mixture was stirred for 1 hour, sodium fluoroborate (0.17 g.) was added and stirring continued for a further 30 minutes. The solvent was removed.

I. Preparation of metal complexes of Schiff bases of methyl 4,6-O-benzylidene-2-amino-2-deoxy-α-D-allopyranoside.

(a) Methyl N-salicylidene-4,6-O-benzylidene-2-amino-2-deoxy-α-D-allopyranoside (0.65 g.) and cupric acetate .$H_2O$ (0.24 g.) were heated at reflux in ethanol (10 ml.) for 10 minutes. The ethanol was evaporated off and the residue was dissolved in toluene. The toluene solution was washed with saturated aqueous sodium bicarbonate solution, the water, dried and evaporated. The residue was washed with methanol and dried to give a binuclear copper complex of methyl N-salicylidene-4,6-O-benzylidene-2-amino-2-deoxy-α-D-allopyranoside (0.3 g.) as a deep green solid.

(b) Methyl 4,6-O-benzylidene-2-amino-2-deoxy-α-D-allopyranoside (0.7 g.) in methanol (10 ml.) was added dropwise with stirring over 1 hour to a suspension of $Cu^{II}$bis (salicylaldehyde) (0.38 g.) in methanol (10 ml.). The reaction mixture was stirred for 1 hour and a solid was filtered off. The filtrate was evaporated to dryness to leave a mononuclear copper complex of methyl N-salicylidene-4,6-O-benzylidene-2-amino-2-deoxy-α-D-allopyranoside as a green solid (0.5 g.).

J. Preparation of metal complexes of Schiff bases of methyl 2-amino-B 2-deoxy-β-D-glucopyranoside.

(a) Methyl N-salicylidene-2-amino-2-deoxy-β-D-glucopyranoside (1.15 g.) and $Cu^{II}$bis(salicylaldehyde) (0.4 g.) were stirred in methanol (10 ml.) for 2 hours. The reaction mixture was evaporated to dryness to leave a mononuclear copper(II) complex of methyl N-salicylidene-2-amino-2-deoxy-β-D-glucopyranoside.

(b) Methyl N-(2-hydroxy-1-naphthylidene)-2-amino-2-deoxy-β-D-glucopyranoside (1.40 g.) and $Cu^{II}$bis(salicylaldehyde) (0.4 g.) were stirred in methanol (10 ml.) for 2 hours. The reaction mixture was evaporated to dryness to leave a mononuclear copper(II) complex of methyl N-(2-hydroxy-1-naphthylidene)-2-amino-2-deoxy-β-D-glucopyranoside.

(c) Cupric chloride 0.2$H_2O$ (0.17 g.) in water (4 ml.) was added to methyl N-(2-pyridinylidene)-2-amino-2-deoxy-β-D-glucopyranoside (1.20 g.) in methanol (10 ml.). The reaction mixture was stirred for 1 hour, sodium fluoroborate (0.4 g.) was added and stirring was continued for a further hour. The reaction mixture was evaporated to dryness to leave a mononuclear copper(II) complex of methyl N-(2-pyridinylidene)-2-amino-2-deoxy-β-D-glucopyranoside.

K. Preparation of metal complexes of Schiff bases of methyl 2-amino-2-deoxy-α-D-glucopyranoside.

(a) Methyl N-salicylidene-2-amino-2-deoxy-α-D-glucopyranoside (0.85 g.) and $Cu^{II}$bis(salicylaldehyde) (0.3 g.) were stirred in methanol for 2 hours. The reaction mixture was evaporated to dryness to leave a mononuclear copper(II) complex of methyl N-salicylidene-2-amino-2-deoxy-α-D-glucopyranoside.

(b) Cupric chloride 0.2$H_2O$ (0.12 g.) in water (3 ml.) was added to methyl N-(2-pyridinylidene)-2-amino-2-deoxy-α-D-glucopyranoside (0.90 g.) in methanol (3 ml.). The reaction mixture was stirred for 1 hour, sodium fluoroborate (0.3 g.) was added and stirring was continued for a further 2 hours. The reaction mixture was evaporated to dryness to leave a mononuclear copper(II) complex of methyl N-(2-pyridinylidene)-2-amino-2-deoxy-α-D-glucopyranoside.

The invention is illustrated by the following Examples, in which all percentages are by weight.

EXAMPLES 1–5

These Examples illustrate the use of novel metal complex catalysts of class (ii) in the reaction of a diazoacetate ester with a halogenated diene of general formula (II). 1,1-Dichloro-4-methyl-1,3-pentadiene (DCMP-1,3) (9.1 g.) (60 m.mole) was added to a measured quantity of the appropriate catalyst ($\equiv$0.04 mg atoms of metal) under an atmosphere of nitrogen. A solution of (0.25 ml) containing dodecane (1.76 m.mole per ml) in a chlorinated solvent (1,2-dichloroethane or 1,1,2,2-tetrachloro-ethane) was added as a glc internal standard. The mixture was then heated to 50° C. with stirring under an atmosphere of nitrogen. A solution containing DCMP-1,3 (60 m mole) and diazoacetic acid ethyl ester (DAE) (15 m mole) in toluene (2 ml) was then added to the stirred mixture over a period of 20 hours. Nitrogen evolution was monitored throughout the reaction and small samples of the reaction mixture were withdrawn from time to time for glc analysis. % yields were determined in terms of moles of ethyl 2,2-dimethyl-3(2,2-dichlorovinyl)cyclopropanecarboxylate (PAE) per mole of nitrogen evolved (i.e. mole of diazoacetic ester decomposed).

The solvent for the reaction (1,2-dichloroethane) was removed using a rotary evaporator and the PAE isolated by column chromatography using an alumina (type H) column. Unreacted DCMP-1,3 was washed from the column by elution with petroleum ether (40°–60° C.) and the PAE subsequently recovered by elution with diethyl ether. Diethyl fumarate and diethyl maleate co-products remained in the column.

The PAE was hydrolysed with ethanolic NaOH to give the free acid which was treated with thionyl chloride to give the acid chloride. This was reacted with 2-d-octanol to give a mixture of four diastereoisomers. These were analysed by glc on a 15 ft column of 5% LAC-2R-446 on Embacel at 125° C. The results are set out in Table 1 and 2.

From Table 1 is can be seen that an enantiomeric excess of the IR isomers is obtained when the reaction of 1,1-dichloro-4-methyl-1,3-pentadiene with diazoacetic acid ethyl ester is catalysed by a mononuclear copper complex of a Schiff base having at C2 of the monosaccharide the configuration specified in general formula (XIX). From Table 2 it can be seen that an enantiomeric excess of the IS isomers is obtained when the same reaction is catalysed by a mononuclear copper complex of a Schiff base having at C2 of the monosaccharide the configuration opposite to that specified in general formula (XIX).

TABLE 1

| Catalyst | Method of Catalyst Preparation | Yield of PAE$^a$ (%) | Isomer Ratio (%) | Excess of 1R's (%)$^b$ |
|---|---|---|---|---|
| Mononuclear Cu(II) complex of the Schiff base derived from salicylaldehyde and methyl 4,6-O-benzylidene-2-amino-2-deoxy-α-D-allopyranoside (see D(a) above) | C | 43 | 25 (1R cis) 18 (1S cis) 32 (1R trans) 25 (1S trans) | 14 |
| Mononuclear Cu(II) complex of the Schiff base derived from salicylaldehyde and methyl 4,6-O-benzylidene-2-amino-2-deoxy-α-D-allopyranoside (see I(b) above) | B | 17 | 24 (1R cis) 20 (1S cis) 29 (1R trans) 27 (1S trans) | 6 |
| Mononuclear Cu(II) complex of the Schiff base derived from 2-pyridinecarboxaldehyde and methyl 2-amino-2-deoxy-β-D-glucopyranoside (see F(b) above) | A | 49 | 19 (1R cis) 17 (1S cis) 34 (1R trans) 30 (1S trans) | 6 |

$^a$based on N$_2$ evolved.
$^b$1R cis + 1R trans − 1S cis − 1S trans.
A: The Schiff base was reacted with a Cu(II) salt.
B: The monosaccharide derivative was reacted with bis(salicylaldehydato)copper (II).
C: The Schiff base was reacted with bis(salicylaldehydato)copper (II).

TABLE 2

| Catalyst | Method of Catalyst Preparation | Yield of PAE$^a$ (%) | Isomer Ratio (%) | Excess of 1S's (%)$^b$ |
|---|---|---|---|---|
| Mononuclear Cu(II) complex of the Schiff base derived from 2-pyridinecarboxaldehyde and methyl 4,6-O-benzylidene-2-amino-2-deoxy-β-D-altropyranoside (see C(c) above) | A | 14 | 13 (1R cis) 27 (1S cis) 29 (1R trans) 30 (1S trans) | 15 |
| Mononuclear Cu(II) complex of the Schiff base derived from salicylaldehyde and methyl 4,6-O-benzylidene-2-amino-2-deoxy-α-D-altropyranoside (see G(d) above) | B | 44 | 20 (1R cis) 22 (1S cis) 27 (1R trans) 30 (1S trans) | 5 |

$^a$based on N$_2$ evolved
$^b$1S cis + 1S trans − 1R cis − 1R trans
A: The Schiff base was reacted with a Cu(II) salt
B: The Schiff base was reacted with bis(salicylaldehydato)copper (II).

EXAMPLE 6

This Example illustrates the use of a novel chiral metal complex catalyst of class (i) in the reaction of a diazoacetic ester with a halogenated diene of general formula (II).

1,1-Dichloro-4-methyl-1,3-pentadiene (DCMP-1,3) (9.1 g) (60 m mole) was added to the fluoroborate mononuclear copper (II) complex of the Schiff base derived from 2-pyridinecarboxaldehyde and S-2-amino-1,1-di(2-methoxyphenyl)-3-phenyl-1-propanol (65 mg 0.05 mg atoms of copper) under an atmosphere of nitrogen. A solution (0.25 ml) containing dodecane (1.76 m mole per ml) in a chlorinated solvent (1,2-dichloroethane or 1,1,2,2-tetrachloroethane) was added as a glc internal standard. The mixture was then heated to 50° C. with stirring under an atmosphere of nitrogen. A solution containing DCMP-1,3 (60 m mole) and diazoacetic acid ethyl ester (DAE) (15 m mole) in toluene (2 ml) was then added to the stirred mixture over a period of 20 hours. Nitrogen evolution was monitored throughout the reaction and small samples of the reaction mixture were withdrawn from time to time for glc analysis.

% yields were determined in terms of moles of ethyl 2,2-dimethyl-3(2,2-dichlorovinyl)cyclopropane carboxylate (PAE) per mole of nitrogen evolved (i.e. per mole of diazoacetic ester decomposed).

The solvent for the reaction (1,2-dichloroethane) was removed using a rotary evaporator and the PAE isolated by column chromatography using an alumina (type H) column. Unreacted DCMP-1,3 was washed from the column by elution with petroleum ether (40°-60° C.) and the PAE subsequently recovered by elution with diethyl ether. Diethyl fumarate and diethyl maleate co-products remained on the column.

The PAE was hydrolysed with ethanolic NaOH to give the free acid which was treated with thionyl chloride to give the acid chloride. This was reacted with 2-d-octanol to give a mixture of four isomers. These were analysed by glc on a 15 ft column of 5% LAC-2R-446 on Embacel at 125° C. The isomers ratios were:

IR cis—23.5%
IS cis—26.5%
IR trans—21.7%
IS trans—28.3%

From these results it can be seen that an enantiomeric excess of the IS isomers is obtained when the reaction of 1,1-dichloro-4-methyl-1,3-pentadiene with diazoacetic acid ethyl ester is catalysed by a mononuclear copper complex of a Schiff base notionally derived from an S-amino-acid. It is expected that employing in this reaction the metal complex notionally derived from the enantiomeric R-amino acid would produce an enantiomeric excess of the IR isomers of ethyl 3-(2,2-dichlorovinyl)-2,2-dimethyl cyclopropane carboxylate, the precursors of the insecticidally more active isomers.

The catalyst used in this Example was prepared as follows:

(i) Schiff base: (S)-C₆H₅CH₂CHC(OH)(o-C₆H₄OCH₃)₂

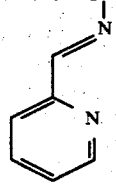

S-2-amino-1,1-bis(o-methoxyphenyl)-3-phenylpropan-1-ol (7.21 g; prepared by the method of A. McKenzie, R. Roger and G. O. Mills, J. Chem. Soc., 1926, 779) and freshly distilled pyridine-2-carboxaldehyde (2.35 g; 1.1 equivalents) were heated together under reflux in anhydrous toluene (50 ml.) for 4 hours. After cooling the reaction mixture to room temperature, the solution was dried over anhydrous magnesium sulphate, filtered, and evaporated in vacuo to afford a viscous brown syrup that was allowed to stand in dichloromethane-light petroleum (b.p. 46°-60° C.) overnight. Light brown cubic crystals separated and were filtered off, washed with cold light petroleum and dried (2.9 g.). The mother liquors were concentrated and two further crops of product were obtained (total yield 5.9 g; 65%). A small portion of the product was recrystallised from methanol and gave light brown crystals melting at 100°-105° C. the ¹H nmr spectrum of the product was consistent with its proposed structure.

(ii) Copper complexes of Schiff base:
    (a) Chloride of the copper complex.

A portion of the Schiff base prepared as described in (i) above (0.828 g.) was dissolved in warm absolute alcohol (30 ml.) and a solution of cupric chloride dihydrate (0.156 g.) in distilled water (5 ml.) was added dropwise over 30 minutes. The solution was stirred at room temperature for 30 minutes and then divided into halves. One half of the solution was evaporated to small hulk and the resulting solid was filtered off, washed with distilled water and dried in vacuo to afford the chloride of the mononuclear copper(II) complex of the Schiff base derived from pyridine-2-carboxaldehyde and S-2-amino-1,1-di(2-methoxyphenyl)-3-phenylpropan-1-ol, which when recrystallised from dichloromethane/hexane melted at 170° C. with decomposition.

| Elemental analysis for $C_{58}H_{56}O_6N_4CuCl_2$: | | | | |
|---|---|---|---|---|
| | C | H | N | Cl | Cu |
| Found: | 64.73 | 5.95 | 5.30 | 8.65 | 7.80 |
| Calculated | 67.01 | 5.43 | 5.39 | 6.82 | 6.11 |

(b) Fluoroborate of the copper complex.

A solution of sodium fluoroborate (0.1 g.) in distilled water (5 ml.) was added to the other half of the solution. The mixture was evaporated to small bulk and the resulting solid was filtered off, washed with distilled water and dried in vacuo to afford the fluoroborate of the mononuclear copper(ii) complex of the Schiff base derived from pyridine-2-carboxaldehyde and S-2-amino-1,1-di-(2-methoxyphenyl)-3-phenylpropan-1-ol having melting point 140°-142° C. (decomposition).

| Elemental analysis for $C_{58}H_{56}O_6N_4CuB_2F_8$: | | | | |
|---|---|---|---|---|
| | C | H | N | Cu |
| Found: | 59.52 | 4.28 | 4.61 | 5.7 |
| Calculated | 60.98 | 4.95 | 4.91 | 5.6 |

EXAMPLE 7

This Example illustrates the use of a novel chiral metal complex catalyst of class (iii) in the reaction of a diazoacetic acid ester with a halogenated diene of general formula (II).

1,1-Dichloro-4-methyl-1,3-pentadiene (3.0 g, 20 mM) and the catalyst (prepared as described below) (0.096 g, 0.1 mM) were stirred together in toluene (10.0 ml) at 75° C. under an atmosphere of nitrogen. A solution comprising the diene (3.0 g, 20 mM), ethyl diazoacetate (5.8 ml of a standard toluene solution containing 8.0 mM of the azo compound) and toluene (10.0 ml) was added dropwise at the rate of 1.2 ml/h.

After 20 hours the volume of nitrogen evolved (160 ml) was virtually quantitative for total consumption of the diazoacetate. Glc analysis of the 2-d-octyl esters gave the following data:

Yield of cyclopropane products (based on 100% consumption of diazoacetate) 37%

Cis: trans ratio 42:58
Isomer distribution
  cis—IR 24%
  cis—IS 18%
  trans—IR 30%
  trans—IS 28%

The catalyst used in this Example was prepared as follows:

(i) Schiff base

A mixture of S-2-amino-1,1-di(2-methoxyphenyl)-3-phenyl-1-propanol (2.01 g.:5.54 m mole) (prepared by the method of A. McKensie, R. Roger and G. O. Wills, *J. Chem. Soc.*, 1926, 779) and pyridine-2,6-dicarboxaldehyde (0.374 g.:2.77 m mole) (prepared by the method of E. Papadopoulos, A. Jarrow and C. H. Issidorides, *J. Org. Chem.*, 1966, 31 615) was heated at reflux in absolute alcohol (100 ml.) for 3 hours. After this time thin layer chromatography on silica gel using ether as eluant indicated a single product and no starting materials. Decolourising charcoal was added to the reaction mixture which was then heated for a further 1 hour. The reaction mixture was filtered and the filtrate was evaporated to approximately one-third of its volume. Addition of n-hexane to the concentrated filtrate gave a precipitate which was filtered off and dried (1.51 g; 65% yield) m.pt. 160°-161° C. The $^1$Hnmr spectrum of the precipitate was consistent with the structure:

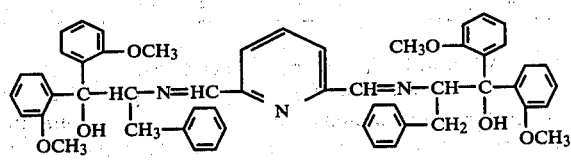

(ii) Copper (II) chloride derivative of Schiff base:

To a solution of the chiral Schiff base (0.447 g.:5.42 m mole) prepared as described in (i) above, in warm ethanol (20 ml.) was added dropwise with stirring over 15 minutes to a solution of copper (II) chloride dihydrate (0.092 g.:5.4 m mole) in water (5 ml.). During the addition the colour of the reaction mixture changed from pale yellow to green. The reaction mixture was evaporated to dryness and the resulting green solid was recrystallised from dichloromethane-hexane to give crystals (0.47 g.:90% yield), m.pt. 166°-168° C. (dec.).

We claim:

1. A process for the preparation of a compound of the formula:

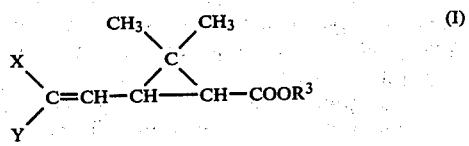

wherein $R^3$ is lower alkyl, 3-phenoxybenzyl, α-cyano-3-phenoxybenzyl or α-ethynyl-3-phenoxybenzyl group, and X and Y, which may be the same or different, are fluorine, chlorine, bromine, lower alkyl or $Q(CF_2)_m$—, in which Q is hydrogen, fluorine or chlorinne and m is 1 or 2, or

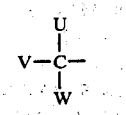

in which each of U, V and W are independently hydrogen, fluorine or chlorine except that where one of X and Y is a group of formula $Q(CF_2)_m$— where Q is as defined above, the other of X and Y is fluorine, chlorine or bromine or a group

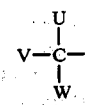

as previously defined, characterised in that a compound having the formula:

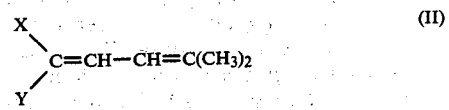

is reacted with an alkyl diazoacetate $N_2CH \cdot COOR^3$, $R^3$, X and Y having the previously defined meanings, in the presence of a catalyst which is the transition metal complex of a chiral Schiff base selected from the group consisting of the compound derived from pyridine-2-carboxaldehyde and S-2-amino-1,1-di-(2-methoxyphenyl)-3-phenylpropan-1-ol, the compound derived from pyridine-2,6-dicarboxaldehyde and S-2-amino-1,1-di-(2-methoxyphenyl)-3-phenylpropan-1-ol, methyl N-salicylidene-4,6-O-benzylidene-2-amino-2-deoxy-alpha-D-altropyranoside, methyl N-(2-hydroxy-1-napthylidene)-4,6-O-benzylidene-2-amino-2-deoxy-alpha-D-altropyranoside, methyl N-(2-pyridinylidene)-4,6-O-benzylidene-2-amino-2-deoxy-alpha-D-altropyranoside, methyl N-salicylidene-4,6-O-benzylidene-2-amino-2-deoxy-beta-D-altropyranoside, methyl N-(2-hydroxy-1-naphthylidene)-4,6-O-benzylidene-2-amino-2-deoxy-beta-D-altropyranoside, methyl N-(2-pyridinylidene)-4,6-O-benzylidene-2-amino-2-deoxy beta-D-altropyranoside, methyl N-salicylidene-4,6-O-benzylidene-2-amino-2-deoxy-alpha-D-allopyranoside, methyl N-(2-pyridinylidene)-4,6-O-benzylidene-2-amino-2-deoxy-alpha-D-allopyranoside, methyl N-salicylidene-2-amino-2-deoxy-beta-D-glucopyranoside, methyl N-(2-hydroxy-1-naphthylidene)-2-amino-2-deoxy-beta-D-glucopyranoside, methyl N-(2-pyridinylidene)-2-amino-2-deoxy-beta-D-glucopyranoside, methyl N-salicylidene-2-amino-2-deoxy-alpha-D-glucopyranoside and methyl N-(2-pyridinylidene)-2-amino-2-deoxy-alpha-D-glucopyranoside.

* * * * *